United States Patent
Kahlert et al.

(10) Patent No.: US 10,085,653 B2
(45) Date of Patent: Oct. 2, 2018

(54) PULSE TRANSMIT TIME MEASUREMENT DEVICE AND METHOD

(71) Applicant: KONINKLIJKE PHILIPS N.V., Eindhoven (NL)

(72) Inventors: Joachim Kahlert, Aachen (DE); Paul Aelen, Eindhoven (NL); Ronaldus Maria Aarts, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 323 days.

(21) Appl. No.: 14/848,432

(22) Filed: Sep. 9, 2015

(65) Prior Publication Data
US 2016/0066801 A1   Mar. 10, 2016

(30) Foreign Application Priority Data
Sep. 9, 2014 (EP) .................................... 14184071

(51) Int. Cl.
| | | |
|---|---|---|
| A61B 5/0205 | (2006.01) | |
| A61B 5/021 | (2006.01) | |
| A61B 7/04 | (2006.01) | |
| A61B 5/03 | (2006.01) | |
| A61B 5/085 | (2006.01) | |
| A61B 5/087 | (2006.01) | |
| A61B 5/0456 | (2006.01) | |
| A61B 5/0402 | (2006.01) | |
| A61B 5/00 | (2006.01) | |
| A61B 5/11 | (2006.01) | |

(52) U.S. Cl.
CPC ........ *A61B 5/02125* (2013.01); *A61B 5/0053* (2013.01); *A61B 5/0205* (2013.01); *A61B 5/02133* (2013.01); *A61B 5/038* (2013.01); *A61B 5/0402* (2013.01); *A61B 5/085* (2013.01); *A61B 5/682* (2013.01); *A61B 7/04* (2013.01); *A61B 5/0456* (2013.01); *A61B 5/087* (2013.01); *A61B 5/1107* (2013.01); *A61B 5/7257* (2013.01)

(58) Field of Classification Search
CPC . A61B 5/02125; A61B 5/0053; A61B 5/0205; A61B 5/02133; A61B 5/038; A61B 5/0402; A61B 5/085; A61B 5/682; A61B 7/04; A61B 5/0456; A61B 5/087; A61B 5/1107; A61B 5/7257
USPC ....... 600/481, 483, 485, 500–503, 509, 513, 600/538
See application file for complete search history.

(56) References Cited

U.S. PATENT DOCUMENTS

| | | | | |
|---|---|---|---|---|
| 8,069,852 B2 * | 12/2011 | Burton | ..... | A61B 5/04 128/204.18 |
| 8,646,447 B2 * | 2/2014 | Martin | ..... | A61M 16/0051 128/204.18 |
| 2005/0217674 A1 * | 10/2005 | Burton | ..... | A61B 5/04 128/204.23 |
| 2009/0204013 A1 | 8/2009 | Muhlsteff et al. | | |
| 2010/0016694 A1 * | 1/2010 | Martin | ..... | A61M 16/0051 600/324 |
| 2010/0298661 A1 | 11/2010 | McCombie et al. | | |

(Continued)

FOREIGN PATENT DOCUMENTS

WO    WO 2016037982 A2 *    3/2016    ........... A61B 5/0053

*Primary Examiner* — Navin Natnithithadha

(57) ABSTRACT

Proposed is a Pulse Transit Time, PTT, measurement concept wherein a forced oscillation technique, FOT, is used to determine a pulse arrival time at alveoli of the lungs of a patient.

19 Claims, 2 Drawing Sheets

(56) References Cited

U.S. PATENT DOCUMENTS

| | | | | |
|---|---|---|---|---|
| 2011/0192400 A9* | 8/2011 | Burton | ...................... | A61B 5/04 |
| | | | | 128/204.23 |
| 2011/0319724 A1 | 12/2011 | Cox | | |
| 2012/0130205 A1* | 5/2012 | Burton | ...................... | A61B 5/04 |
| | | | | 600/301 |
| 2012/0132202 A1* | 5/2012 | Burton | ...................... | A61B 5/04 |
| | | | | 128/203.14 |
| 2012/0136405 A1* | 5/2012 | Burton | ...................... | A61B 5/04 |
| | | | | 607/18 |
| 2013/0123617 A1 | 5/2013 | Sola I Caros et al. | | |
| 2014/0116442 A1* | 5/2014 | Martin | .................. | A61B 5/4818 |
| | | | | 128/204.23 |

* cited by examiner

PULSE TRANSMIT TIME MEASUREMENT DEVICE AND METHOD

FIELD OF THE INVENTION

This invention relates to monitoring vital signs of a subject, and more particularly to measuring the pulse transit time (PTT) of a subject.

BACKGROUND OF THE INVENTION

There is an increasing demand for continuous or regular monitoring of a patient's vital signs, for assessing cardiovascular function for example. The use of electrocardiograms (ECGs), blood pressure (BP) measurement systems and pulse oximeters is therefore widely known.

Non-invasive measurement of BP using cuff-based methods provides adequate data for many applications in medicine. However, cuff-based methods exhibit disadvantages which can limit their use in certain clinical situations. First, a continuous measurement of blood pressure is not possible, since a pause of at least 1-2 min between two BP measurements is necessary to avoid errors in the measurement. Therefore, short-term changes in BP cannot be detected. Furthermore, the inflation of the cuff may disturb the patient and the consequences of these disturbances are alterations of the BP. Both problems are, for example, important when investigating BP fluctuations during sleep.

A known alternative approach for a continuous, non-invasive and indirect measurement of BP is based on changes in pulse wave velocity (PWV). PWV is the speed of a pressure pulse propagating along the arterial wall. Typically, a relation of blood pressure and PWV in arteries is expressed by the Moens-Korteweg-relation, which can be derived from hydrodynamic theory:

$$c = \sqrt{\frac{hE_t}{2\rho R}} \quad \text{(Eq. 1)}$$

Equation 1: Moens-Korteweg-Equation Often Used to Describe the Relation of Pulse-Wave-Velocity and Blood Pressure where: c=pulse wave velocity, $E_t$=tangential elasticity module, $\rho$=density, R=radius of artery, h=artery wall thickness.

PWV can be calculated from pulse transit time (PTT). PTT is the time a propagating wave takes on the same cardiac cycle between two separate arterial sites. PTT has been shown to be quasi-linear to low BP values, but increases exponentially at higher pressures. Typical known set-ups for measuring PTT include:
1. ECG- and Photoplethysmography (PPG): Wherein PTT is given by the time-difference between R-peak and characteristic points in PPG. The PPG can be measured at various positions on the body e.g. ear or finger;
2. ECG and bio-impedance measurement at arm (impedance plethysmography (IPG)): Wherein PTT is given by the time-difference between an R-peak of an ECG signal and characteristic points in the IPG;
3. Impedance Cardiography (ICG) of the thorax and bio-impedance measurement at arm (IPG): Wherein PTT is given by the time-difference between characteristic points in the ICG and characteristic points in the IPG; and
4. Impedance plethysmogram (IPG1) at a first position on an arm and bio-impedance measurement at a second position on an arm (IPG2): Wherein PTT is given by the time-difference between characteristic points in the IPG1 and characteristic points in the IPG2.

However, when clinical standard sensors or methodologies are used, the above methods for measuring PTT have several disadvantages, especially for personal healthcare applications. State of the art sensors, such as finger or ear sensors, measuring a photoplethysmogram or bio-impedance methodologies are an inconvenience in normal life requiring PPG sensors or special medical electrodes that must be glued to the skin. Accordingly, such methodologies for measuring PTT are not suitable for long term continuous or regular monitoring of a patient's BP.

SUMMARY OF THE INVENTION

The invention is defined by the claims.

According to an aspect of the invention there is provided a PTT measurement method characterised by comprising the step of: using a forced oscillation technique (FOT) to determine a pulse arrival time at alveoli of the lungs of a patient.

Embodiments are based on the realisation that a FOT can be used to determine when a pulse wave travelling through the pulmonary arteries arrives at alveoli of a patient's lungs. Such use of a FOT may therefore enable non-invasive, unobtrusive acoustical PTT measurements. Unlike conventional methods for determining a pulse wave arrival time at an arterial site, the proposed use of a FOT to determine a pulse arrival time at the alveoli of a patient's lungs may allow for continuous or regular monitoring of (pulmonary) BP in the pulmonary arteries at the right side of the heart. Also, unlike conventional methods which rely on obtrusive or invasive techniques, embodiments may use non-invasive techniques suitable for continuous monitoring of BP. Embodiments may therefore be employed in the field of monitoring vital signs of a patient, and more particularly in the field of monitoring BP at home, at sleep, or at a medical centre.

Embodiments may comprise the preceding step of: determining a pulse start time. Further, the step of determining a pulse start time may comprise using a phonocardiograph to determine a point in time when the pulmonary valve of the patient's heart opens. For example, a phonocardiograph may be used to identify a time when the pulmonary heart valve opens and when the blood pressure wave runs into the pulmonary artery filling up the pulmonary arteries.

The step of determining a pulse start time may otherwise (or additionally) comprise using an ECG to determine a point in time when the right ventricle of the patient's heart contracts. For example, an R-peak in an ECG signal may be used to identify a pulse start time.

Embodiments may therefore use various techniques to determine a pulse start time.

In an embodiment, a PTT may be calculated based on the determined pulse start time and pulse arrival time. For example, a PPT may be calculated based on the time difference between the determined pulse start time and the determined pulse arrival time. In other words, a PPT may be calculated based on the time difference between the time of opening of the pulmonary valve and the time of arrival of the pressure wave at alveoli of the lungs.

According to an aspect of the invention, there may be provided a BP measurement method comprising a PTT measurement method according to an embodiment. Unlike conventional BP measurement methods (which only enable a PTT measurement of the pulse wave created by the contraction of the left ventricle), embodiments may be employed to measure the blood pressure in the pulmonary arteries at the right side of the heart. Thus, there may be proposed a method for monitoring pulmonary BP in a non-invasive and unobtrusive manner. Embodiments may therefore be of particular relevance to applications in which it is advantageous to be able to enable an unobtrusive diagnostic modality for regularly or continuously measuring PTT and/or BP.

According to yet another aspect of the invention, there is provided a PTT measurement device comprising an FOT unit adapted to perform a forced oscillation technique to determine a pulse arrival time at the alveoli of the lungs of a patient.

Unlike conventional sensors placed at the finger, arm or ear, which are not suitable to measure the PTT in a pulmonary artery when the pulse wave is created by the contraction of the right ventricle, embodiments provide a PTT measurement device that may be used to measure the PTT in a pulmonary artery. Put another way, there may be provided an acoustical diagnostic system that may be used to measure the PTT of a pressure wave in the pulmonary arteries.

In an embodiment, the PTT measurement device may further comprise a pulse detection unit adapted to determine a pulse start time. Such a pulse detection unit may comprise phonocardiograph apparatus adapted to determine a point in time when the pulmonary valve of the patient's heart opens. Such a pulse detection unit may otherwise (or additionally) comprise an electrocardiogram apparatus adapted to determine a point in time when the right ventricle of the patient's heart contracts.

An embodiment may further comprise a processing unit adapted to calculate a PTT based on the determined pulse start time and pulse arrival time.

According to another aspect of the invention, there may be provided a BP measurement device comprising a PTT measurement device according to an embodiment. Such a device may be used in the office of a General Practitioner in a general health check-up and/or by a pulmonologist for assessing respiratory system performance. Also, an embodiment may be used by a cardiologist to measure/monitor pulmonary BP.

Embodiments may be used in a stand-alone device or may be integrated with existing polysomnography systems, polygraphy systems, cardiac monitoring systems, ventilation systems and/or spirometers.

Proposed embodiments may also be used by a sleep physician to monitor BP in a sleep study. A device according to an embodiment may therefore be integrated in a continuous positive airway pressure (CPAP) device to monitor BP during sleep at home.

BRIEF DESCRIPTION OF THE DRAWINGS

Examples of the invention will now be described in detail with reference to the accompanying drawings, in which.

DETAILED DESCRIPTION OF THE EMBODIMENTS

Embodiments employ the concept of using an acoustical diagnostic system/method to identify a pulse pressure wave arrival time in the alveoli of a patient. The invention may therefore provide for the measurement of PTT using a FOT. Such use of a FOT may therefore enable a non-invasive, unobtrusive acoustical way of measuring the PTT of a pulse pressure wave in the pulmonary arteries. Embodiments may therefore be useful for the field of monitoring BP.

The diagrams are purely schematic and it should therefore be understood that the dimensions of features are not drawn to scale. Accordingly, the illustrated thickness of any of the layers should not be taken as limiting. For example, a first layer drawn as being thicker than a second layer may, in practice, be thinner than the second layer.

Figure 1:
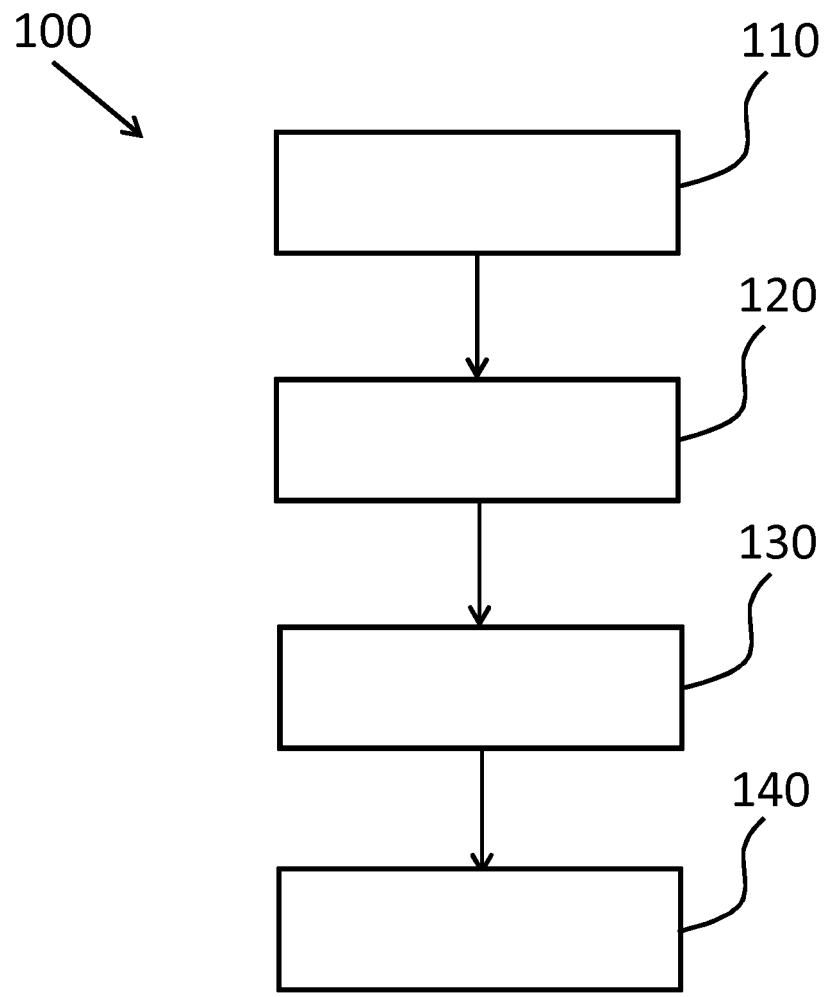
FIG. 1 depicts a flow diagram of a PPT measurement method according to an embodiment.

Referring to FIG. 1, there is depicted a flow diagram of a PTT measurement method 100 according to an embodiment.

The method begins with step 110 wherein a pulse start time T1 is determined. The pulse start time T1 may be considered as being indicating the time of a heartbeat and may be identified, for example, as the time at which the pulmonary heart valve opens and the blood pressure wave runs into the pulmonary artery filling up the pulmonary arteries. The pulse start time T1 may be identified by using a phonocardiograph to determine a point in time when the pulmonary valve of the heart opens.

A phonocardiograph is a widely known system in the field of cardiology and is typically used to monitor and diagnose (in real time) the contraction of heart chambers and the opening of the cardiac valves. Thus, a phonocardiograph system can be used to identify a time at which the pulmonary heart valve opens and the blood pressure wave runs into the pulmonary artery filling up the pulmonary arteries.

Phonocardiography is a well-known diagnostic technique that creates a graphic record (or phonocardiogram) of the sounds and murmurs produced by the contracting heart, including its valves and associated great vessels. The phonocardiogram is obtained either with a chest microphone or with a miniature sensor in the tip of a small tubular instrument that is introduced via the blood vessels into one of the heart chambers. The phonocardiogram usually supplements information obtained by listening to body sounds with a stethoscope (auscultation). It may therefore be of special diagnostic value when performed simultaneously with measurement of the electrical properties of the heart (electrocardiography) and pulse rate.

In step 120, a pulse arrival time T2 at the alveoli of the lungs of a patient is determined. In this embodiment, the pulse arrival time T2 is the time at which the blood pressure wave arrives at the alveoli of a patient and is determined using a FOT. FOT is known in pulmonology to measure the respiratory resistance of lung and upper airway. FOT was introduced by DuBois et al. in 1956 and is an acoustical measurement system/method that has been used for the evaluation of respiratory characteristics in a variety of clinical applications.

The basic principle of FOT is the application of pressure oscillations of small amplitude into the airways of a patient at a higher frequency than the natural breathing frequency. Classically, a loudspeaker generates the pressure oscillations, whereas flow (V) and pressure (P) signals are recorded close to the airway opening by means of a pneumotachograph and a pressure transducer, respectively. The complex relationship between applied pressure and resulting flow, called impedance (Zrs), is determined by the mechanical properties of the airways, the lung tissue and the chest wall. Zrs, in general, is dependent on the frequency of oscillation. In a simplistic model, the in-phase relationship between pressure and flow, the resistance or real part of impedance (Rrs), is determined by the resistive properties of the respiratory system. The 90-degree out-of-phase relationship, reactance or imaginary part of impedance (Xrs), is determined by the elastic properties of the respiratory system at low frequency and by the inertive elements at high frequency. There are two different ways of applying FOT. To study the frequency-dependent behaviour of Zrs, multiple frequencies can be applied simultaneously after which a Fast Fourier transform identifies the different frequencies applied. Alternatively, a monosinusoidal pressure oscillation can be applied which enables a cycle-per-cycle analysis of the pressure and flow signals (one cycle=1/(frequency of oscillation)) so that the time-dependent changes of Zrs can be monitored optimally. The latter methodology results in a high time resolution of information and allows tracking of changes of Zrs along the breathing cycle and changes of Zrs along the cardiac cycle, in particular the change of Zrs at the arrival of the pulmonary blood pulse wave.

Next in step 130, the PTT ($T_{PTT}$) for same cardiac cycle is calculated based on the pulse start time determined in step 110 and the pulse arrival time determined in step 120. Thus, for the same cardiac cycle (e.g. for a single pulse or heartbeat), the PTT is calculated based on the time taken for a pulse pressure wave to travel between two (pulmonary) arterial sites, wherein the first arterial site is the pulmonary heart valve or artery and the second arterial site is alveoli of the lungs. More specifically, in step 130 of this embodiment, the PTT ($T_{PTT}$) is calculated based on the time difference between the pulse start time T1 and the pulse arrival time T2. An equation for this calculation may therefore be (Equation 2):

$$T_{PTT}=T2-T1 \quad (\text{Eq. 2}),$$

wherein: $T_{PTT}$ is the PTT for a cardiac cycle of interest; T1 is the pulse start time for the cardiac cycle of interest; and T2 pulse arrival time at the alveoli of the lungs.

Finally, in step 140, the calculated value of PTT ($T_{PTT}$) is output (for example, to a BP monitoring device).

The method may then return to step 110 for the purpose of calculating/measuring the PTT of a subsequent cardiac cycle. It will therefore be appreciated that the proposed method may be executed repeatedly on a beat-by-beat basis so as to enable continuous measurement and monitoring of PTT for a patient.

Figure 2:
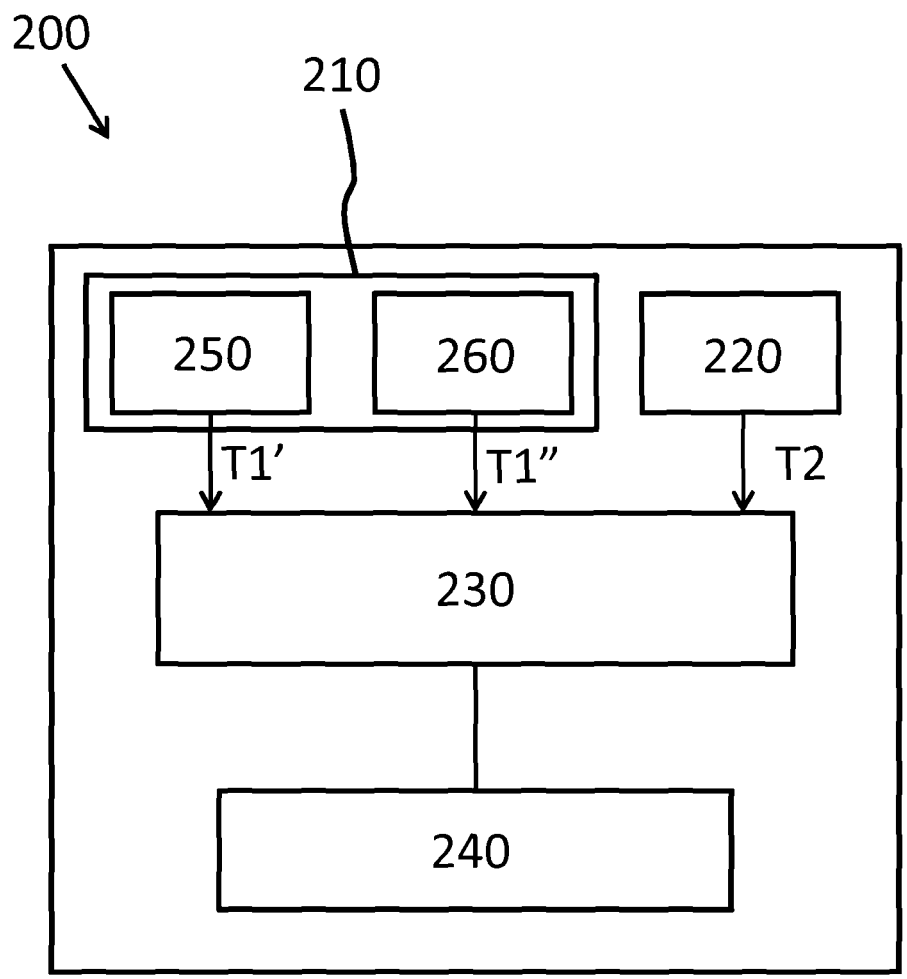
FIG. 2 depicts a schematic block diagram of a measurement device according to an embodiment.

Referring now to FIG. 2, there is depicted a PTT measurement device 200 according to an embodiment.

The PTT measurement device 200 comprises: a pulse detection unit 210 adapted to determine a pulse start time; a FOT unit 220 adapted to perform a FOT to determine a pulse arrival time; a processing unit 230; and an output interface 240.

Here, the pulse detection unit 210 comprises: phonocardiograph apparatus 250 adapted to determine a point in time T1' when the pulmonary valve of the patient's heart opens; and electrocardiogram apparatus 260 adapted to determine a point in time T1" when the right ventricle of the patient's heart contracts. The determined values of T1' and T1" may be different, due to differences in the measurement techniques and/or accuracies for example. Both such values of T1' and T1" may therefore be used to determine a pulse start time T1, for example by using T1" as an error checking vale for T1' (or vice versa) and/or by extrapolating between the value of T1' and T1".

The FOT unit 220 comprises FOT acoustical measurement apparatus adapted to determine a pulse arrival time T2 at the alveoli of the lungs of the patient.

The values of T1' and T1" obtained by the pulse detection unit 210, and the value of T2 obtained by the FOT unit 220, are provided to the processing unit 230.

The processing unit 230 is adapted to calculate a PTT based on the values of T1', T1" and T2 it receives (from the pulse detection unit 210 and the FOT unit 220) for the same cardiac cycle. More specifically, the processing unit 230 calculates the PTT ($T_{PTT}$) based on the time difference between the pulse start time T1 and the pulse arrival time T2, wherein the pulse start time T1 is determined from the values of T1' and T1". The processing unit 230 then provides the calculated value of PTT ($T_{PTT}$) to the output interface 240.

In this embodiment, the output interface 240 comprises a communication interface which is adapted to communicate calculated values of PTT ($T_{PTT}$) to another apparatus (such as a BP calculation or monitoring device) for further processing and/or use.

It will be understood, however, that processing unit 230 may be further adapted to calculate a PWV value and/or a BP value based on a calculated value of PTT ($T_{PTT}$). This may be done, for example, by determining a value of PWV from the calculated value of PTT and then calculating a corresponding BP value from the PWV value (using a relationship such as the Moens-Korteweg-relation for example). Such a value of PWV and/or BP may therefore be provided by the processing unit 230 to the output interface 240.

Accordingly, in a slightly modified embodiment, the output interface may comprise a display device adapted to display a BP value that has been calculated by the processing unit. By arranging the device to obtain a PTT measurement for each heartbeat, the processing unit may therefore be adapted to determine a corresponding BP value for each heart beat and output such BP values, thereby enabling continuous monitoring of the patient's BP.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or an does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A method comprising the steps of:
   determining a pulse start time;
   using a forced oscillation technique to determine a pulse arrival time at alveoli of lungs of a patient, the determination of the pulse arrival time based on determining a change in impedance at the alveoli, the change in impedance based on a blood pressure wave arriving at the alveoli;
   determining a pulse transit time based on the pulse start time and the pulse arrival time; and
   transmitting the pulse transit time to an output interface for monitoring of a cardiovascular function for the patient.

2. The method of claim 1, wherein the step of determining a pulse start time comprises:
   using a phonocardiograph to determine a point in time when a heart pulmonary valve of the patient opens.

3. The method of claim 1, wherein the step of determining a pulse start time comprises:
   using an electrocardiogram to determine a point in time when a right ventricle of a heart of the patient contracts.

4. The method of claim 1, wherein using a forced oscillation technique comprises:
applying pressure oscillations into airways of the patient at a higher frequency than a natural breathing frequency of the patient.

5. The method of claim 1, further comprising measuring blood pressure based on the pulse transit time.

6. A pulse transit time measurement device, comprising:
a pulse detection unit adapted to determine a pulse start time;
a forced oscillation technique unit adapted to perform a forced oscillation technique to determine a pulse arrival time at alveoli of the lungs of a patient, the determination of the pulse arrival time based on determining a change in impedance at the alveoli, the change in impedance based on a blood pressure wave arriving at the alveoli; and
a processing unit adapted to determine the pulse transit time based on the pulse start time and the pulse arrival time and transmit the pulse transit time to an output interface for monitoring of a cardiovascular function for the patient.

7. The pulse transit time measurement device of claim 6, wherein the pulse detection unit comprises:
a phonocardiograph apparatus adapted to determine a point in time when a heart pulmonary valve of the patient opens.

8. The pulse transit time measurement device of claim 6, wherein the pulse detection unit comprises:
an electrocardiogram apparatus adapted to determine a point in time when a right ventricle of a heart of the patient contracts.

9. The pulse transit time measurement device of claim 6, wherein the forced oscillation technique unit comprises an apparatus adapted to apply pressure oscillations into airways of the patient at a higher frequency than a natural breathing frequency of the patient.

10. A system, comprising:
a pulse detection unit adapted to determine a pulse start time;
a forced oscillation technique unit adapted to perform a forced oscillation technique to determine a pulse arrival time at alveoli of the lungs of a patient, the determination of the pulse arrival time based on determining a change in impedance at the alveoli, the change in impedance based on a blood pressure wave arriving at the alveoli; and
a processing unit adapted to determine the pulse transit time based on the pulse start time and the pulse arrival time and transmit the pulse transit time to an output interface for monitoring of a cardiovascular function for the patient.

11. The system of claim 10, wherein the pulse detection unit comprises:
a phonocardiograph apparatus adapted to determine a point in time when a heart pulmonary valve of the patient opens.

12. The system of claim 10, wherein the pulse detection unit comprises:
an electrocardiogram apparatus adapted to determine a point in time when a right ventricle of a heart of the patient contracts.

13. The system of claim 10, wherein the forced oscillation technique-unit comprises an apparatus adapted to apply pressure oscillations into airways of the patient at a higher frequency than a natural breathing frequency of the patient.

14. The system of claim 10, wherein the system comprises a blood pressure measurement device comprising the pulse detection unit, the forced oscillation technique unit, and the processing unit.

15. The system of claim 10, wherein the system comprises a cardiac monitoring system comprising the pulse detection unit, the forced oscillation technique unit, and the processing unit.

16. The system of claim 10, wherein the system comprises a spirometer comprising the pulse detection unit, the forced oscillation technique unit, and the processing unit.

17. The method of claim 1, wherein transmitting comprises transmitting the pulse transit time on a beat-by-beat basis.

18. The pulse transit time measurement device of claim 6, wherein the pulse transit time is transmitted to the output interface on a beat-by-beat basis.

19. The system of claim 10, wherein the pulse transit time is transmitted to the output interface on a beat-by-beat basis.

* * * * *